United States Patent [19]

DeMarzo

[11] Patent Number: 4,953,552
[45] Date of Patent: Sep. 4, 1990

[54] BLOOD GLUCOSE MONITORING SYSTEM

[76] Inventor: Arthur P. DeMarzo, 2S558 White Birch La., Wheaton, Ill. 60187

[21] Appl. No.: 341,429

[22] Filed: Apr. 21, 1989

[51] Int. Cl.$^5$ .................................................. A61B 5/00
[52] U.S. Cl. ....................................... 128/635; 204/403
[58] Field of Search .......................... 128/635; 204/403

[56] References Cited

U.S. PATENT DOCUMENTS

| | | |
|---|---|---|
| 3,653,841 | 4/1972 | Klein . |
| 4,008,717 | 2/1977 | Kowarski . |
| 4,178,916 | 12/1979 | McNamara . |
| 4,206,755 | 6/1980 | Klein . |
| 4,340,458 | 7/1982 | Lerner et al. . |
| 4,365,637 | 12/1982 | Johnson . |
| 4,366,033 | 12/1982 | Richter et al. . |
| 4,384,586 | 5/1983 | Christiansen . |
| 4,401,122 | 8/1983 | Clark, Jr. . |
| 4,431,004 | 2/1984 | Bessman et al. . |
| 4,436,094 | 3/1984 | Cerami . |
| 4,440,175 | 4/1984 | Wilkins . |
| 4,458,686 | 7/1984 | Clark, Jr. . |
| 4,469,110 | 9/1984 | Slama . |
| 4,477,314 | 10/1984 | Richter et al. . |
| 4,595,011 | 6/1986 | Phillips . |
| 4,627,445 | 12/1986 | Garcia et al. . |
| 4,633,878 | 1/1987 | Bombardieri . |
| 4,637,403 | 1/1987 | Garcia et al. . |
| 4,679,562 | 7/1987 | Luksha . |
| 4,680,268 | 7/1987 | Clark, Jr. . |
| 4,685,463 | 8/1987 | Williams . |
| 4,703,756 | 11/1987 | Gough et al. . |
| 4,711,245 | 12/1987 | Higgins et al. ...................... 128/635 |
| 4,732,153 | 3/1988 | Phillips . |

FOREIGN PATENT DOCUMENTS 0025541  2/1986  Japan .................................... 128/635

OTHER PUBLICATIONS

Shichiri et al., Glycaemic Control In Pancreatectomized Dogs With A Wearable Artificial Endocrine Pancreas, Diabetologia, V. 24, (1983) pp. 179-184.
Turner, et al., Diabetes Mellitus: Biosensors For Research And Management, Biosensors I:85-115 (1985).
Claremont, et al., Potentially-Implantable, Ferrocene-Medicated Glucose Sensor, J. Biomed. Engineering, vol. 8, pp. 272-274 Jul., 1986.
Claremont, et al., Biosensors For Continuous In Vivo Glucose Monitoring, IEEE Engineering in Medicine and Biology Society 10th International Conference, Aug. 1988, 2 pages.

Primary Examiner—Lee S. Cohen
Attorney, Agent, or Firm—Welsh & Katz, Ltd.

[57] ABSTRACT

A blood glucose monitoring system includes a generally planar disposable adhesive patch having a needle type glucose sensor and a second electrode mounted thereon, as well as first and second electrode connectors projecting from an upper surface of the patch and being in electrical connection with the respective electrodes. A microprocessor worn by the user has positive and negative leads for specified connection to the respective electrode connectors and continuously monitors current transmitted by the sensor and displays corresponding average levels of blood glucose on a display panel.

26 Claims, 2 Drawing Sheets

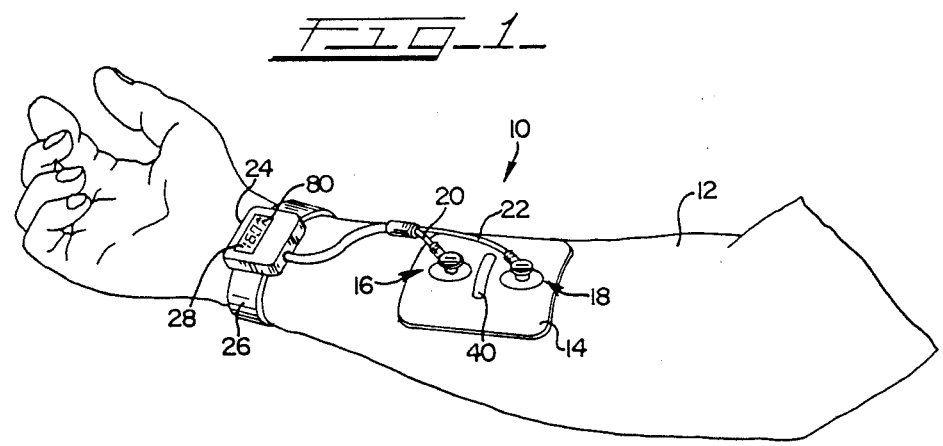
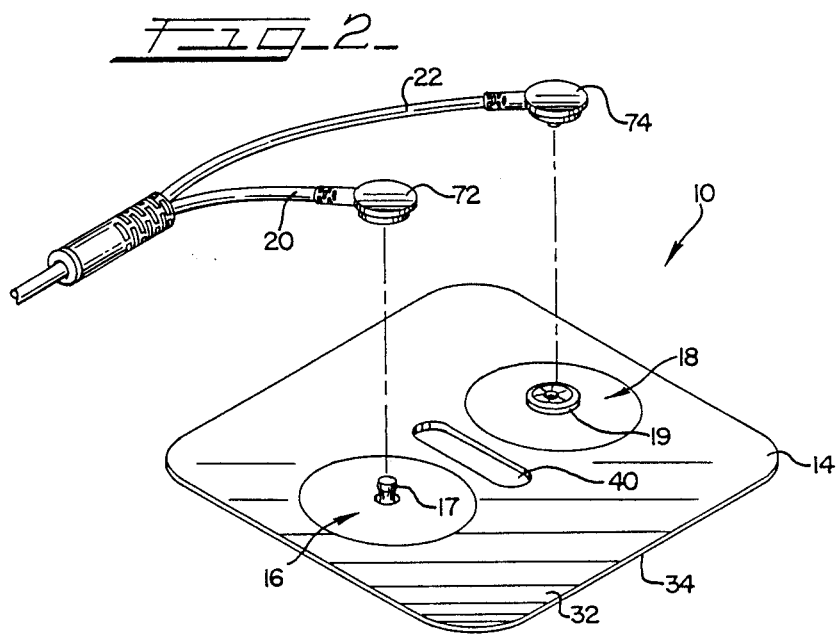

BLOOD GLUCOSE MONITORING SYSTEM

BACKGROUND OF THE INVENTION

The present invention relates to blood glucose monitoring devices, and specifically to a miniaturized blood glucose monitoring system which may be inconspicuously worn by a patient and provides a relatively continuous monitoring of the blood glucose level while causing a minimal invasion into the body.

For diabetic patients, the maintenance of blood glucose levels within a very narrow range (about 3.5–6.5mM) is extremely important, since the brain uses glucose as virtually its only source of energy, and low glucose levels (hypoglycemia) cause mental confusion, and if sustained, coma and death. On the other hand, high blood glucose levels (hyperglycemia) cause unpleasant short term symptoms, such as frequent urination and thirst, and in the long term are probably a major factor in the development of tissue damage in the blood vessels, eyes, kidneys, nerves, etc.

For most diabetics, the injection of insulin is required to maintain blood glucose at acceptable levels. Conventional treatment takes the form of injections of insulin into the subcutaneous tissues of the arms, legs, abdomen or buttocks. Normoglycemia is difficult to achieve in diabetics because insulin injections do not mimic non-diabetic insulin secretion patterns sufficiently closely and there is no feedback control of insulin delivery rates according to the prevailing glucose level. In the last few years there has been an intensive effort to improve metabolic control in diabetics by developing a more physiologically related strategy of insulin administration. Research efforts in this area have been focused on the development of an implantable and inconspicuous glucose sensor for the continuous monitoring of glycemic control. Much of the work to date pertains to sensors which monitor the electric current produced by a reaction of blood glucose with an enzyme such as glucose oxidase.

In such conventional amperometric glucose sensors, the generated hydrogen peroxide or consumed oxygen produced by the catalytic oxidation of glucose by immobilized glucose oxidase is measured. An alternative strategy is to incorporate a redox mediator such as ferrocene in the sensor so that electrons are transferred directly from the prosthetic group of reduced glucose oxidase to a base electrode. The advantages of this latter approach include the fact that the reaction does not require the presence of molecular oxygen and is therefor less prone to changes in tissue oxygen levels.

The design objectives of a continuous glucose monitoring system would include miniaturization for ease of patient comfort and mobility, accuracy, ease of use by younger patients, and minimal bodily invasion, such as at or just below the skin surface.

A miniaturized glucose monitoring system employing subcutaneous needle type glucose sensors has been proposed; however, due to the decrease in accuracy of the platinum needle sensors after about 3 days, the long term use of such a system has been impractical.

Thus, there is a need for a blood glucose monitoring system which is miniaturized to the extent that it can be worn comfortably and inconspicuously by a patient, which is accurate and which provides the capability of readily exchanging needle type glucose sensors and accurately connecting them to a monitoring unit by patients of all ages.

SUMMARY OF THE INVENTION

Accordingly, a blood glucose mOnitoring system is provided, including a disposable patch having a pair of structurally distinguishable electrode connectors and an adhesive on the underside for attachment to the body, a needle type glucose sensor connected to one of the electrode connectors and secured to the patch so that the needle portion depends from the patch underside, and a second neutral electrode for completing the circuit. A microprocessor is also provided, having leads for connection to the respective electrode connectors of the patch. The microprocessor circuitry includes ammeter circuitry for receiving and measuring electrical impulses from the sensor, and is programmed for calculating an average current value over a specified time period and for displaying that value upon an LCD readout. The configuration of the positive and negative electrode connectors on the patch and the lead ends of the microprocessor are such that incorrect electrode connection is prevented. The patch is designed to be readily interchanged, and is disposable, so that after approximately 3 days of use, the patch may be easily removed and replaced with a fresh one. The microprocessor is of miniaturized design so as to be easily worn on the arm of the user.

BRIEF DESCRIPTION OF THE DRAWINGS

FIG. 1 is a front perspective elevational view of the blood glucose monitoring system of the invention mounted upon the forearm of a patient;

FIG. 2 is a front perspective elevational view of the disposable electrode sensor patch of the invention showing the leads from the microprocessing unit exploded away;

DESCRIPTION OF THE PREFERRED EMBODIMENT

Figure 3:
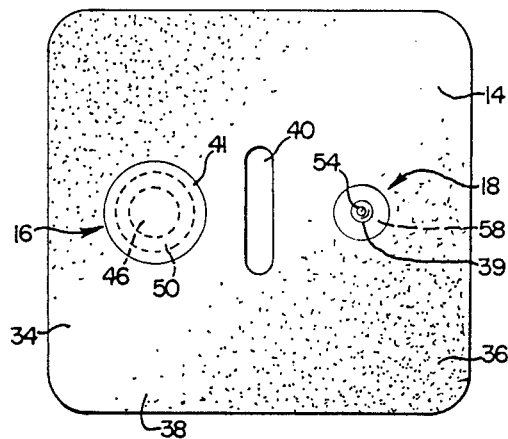
FIG. 3 is a bottom view of the patch depicted in FIG. 2.

Referring now to the drawings, FIG. 1 depicts the blood glucose monitoring system of the invention, designated generally 10. The system 10 of the invention is shown secured to the forearm 12 of a patient, and includes a generally planar disposable patch 14 being releasably adhered to the forearm 12 and having a pair of vertically projecting electrodes generally indicated at 16 and 18 which are in turn connected by leads 20 and 22, respectively, to a microprocessing unit 24. The unit 24 includes means such as a wrist strap 26 for attachment to the forearm or wrist of the patient, as well as an LCD display 28. The display 28 indicates to the patient the level of glucose in the blood and whether that level is increasing, decreasing or trending level.

Figure 4:
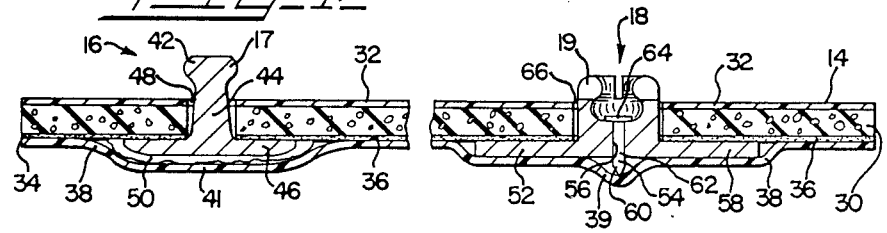
FIG. 4 is a vertical sectional view through the patch of the invention.

Referring now to FIGS. 2, 3 and 4, the disposable patch portion 14 of the invention is depicted in greater detail, and is generally planar and rectangular in peripheral configuration, although other geometric shapes are contemplated for the periphery, provided that sufficient surface area exists to achieve positive adhesion to the patient. The patch 14 includes a central core 30, and may be manufactured of a plurality of flexible nonconductive foam materials such as polyethylene, polyurethane, or polyvinyl chloride. The core 30 includes a top surface 32, a bottom surface 34, both of which serve to close the cells of the foam, and may be created by applying a surface coating or by closing the cells of the foam either thermally or by other conventional procedures. The bottom surface 34 is provided with an adhesive coating 36 covered with an overlying peelable release sheet 38 (best shown in FIG. 4) which prevents the adherence of the patch until desired for application onto the patient.

The top surface 32 of the patch 14 is also provided with the electrodes 16 and 18, which are linearly disposed on the patch with an elongate slot 40 located transversely therebetween to prevent the migration of charges between the respective electrodes. As shown, each electrode 16, 18 has a respective electrode connector 17, 19 with an upwardly projecting portion having a specific structural configuration. More specifically, one of the electrode connectors 17 is provided with a male configuration and the other electrode connector 19 is provided with a female configuration.

Referring now to FIG. 4, the male electrode connector 17 serves as the neutral electrode, and is actually a one-piece electrode and connector, and includes a stud 42 with a shaft 44 and a lower radially flared flanged end 46. The connector 17 is preferably fabricated of molded ABS plastic plated with silver and then chlorided to form the cathode of the present system. Attachment of the connector 17 to the patch 14 is accomplished by inserting the shaft 44 through an opening 48 in the patch until the lower connector end 46 abuts against the bottom 34 of the patch. The connector 46 is secured to the patch 14 by the adhesive coating 36. A layer of conductive gel 50, including potassium chloride, is applied to the flared lower end 46 to ensure electrical continuity with the patient. Although the electrode connector 17, designated a "male" electrode is preferred, the alternative embodiment of a silver chloride electrode having a female configuration and having the above-identified elements may be used.

The electrode 18, referred to as the female electrode, is the anode of the system 10 and basically includes an eyelet 52 and a needle 54. The shaft is made of a plastic such as ABS and is provided with a female receptacle electrode connector portion 19, a vertical throughbore 56 dimensioned to accommodate the needle 54, and a lower flared end 58. The needle 54 is preferably platinum, stainless steel, silver or graphite loaded plastic and has a point or tip 60, a shaft 62 and a flange or head 64. The needle 54 is insert molded into the eyelet 52 so that the head 64 is located at the base of the electrode connector 19.

The release sheet 38 is provided with a thermoformed dimple portion 39 which covers the point 60 of the needle 54 prior to use, protects the needle from physical damage, and seals the coated point 60 of the needle from oxidation and/or other contamination. A second dimple formation 41 may be provided to cover the flared lower end 46 and gel layer 50 of the electrode 16.

Figure 5:
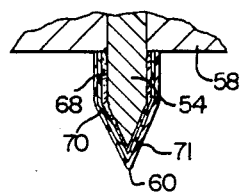
FIG. 5 is a fragmentary diagrammatic vertical sectional view of the needle electrode of the sensor of the invention depicted in FIG. 4.

Electrical continuity is achieved in the electrode 18 through intimate contact of the upper surface of the needle head 64 against the male lead attachment of the lead wire 22. The eyelet 52 is inserted through an opening 66 in the patch 14 and is held there by contact between the flared end 58 and the adhesive coating 36 or other conventional means. To complete the electrode 18, the point 60 of the needle 54 is coated with a ferrocene mediator 68. The needle point 60 is then dipped into a suspension of the enzyme glucose oxidase 70 which will serve as a reactant with the blood glucose to produce electrical current. The coating of ferrocene mediator 68 immobilizes the enzyme. Lastly, a coating of polyurethane 71 is applied over the enzyme coating 70 (coatings 68 and 70 and 71 are best shown in FIG. 5).

More specifically, prior to insertion into the eyelet 52, the needle is placed at room temperature for 10 minutes in 0.2M 1,1'-dimethylferrocene in ethanol and air dried. The needle 54 is then dipped firstly for 90 minutes at room temperature in 0.06 M 1-cyclohexyl-3-(2-morpholinoethyl) carbodiimide p-methyltoluensulfonate in 0.1 M sodium acetate buffer pH 4.5, and then for 18 hours at 4° C. in a solution of glucose oxidase in 0.1 M sodium phosphate buffer pH 7.4. After rinsing in distilled water, the needle is immersed in 2% (v/v) glutaraldehyde in 0.1 M sodium phosphate buffer pH 7.4. A membrane is applied to the needle 54 by dipping into 4% polyurethane.

Figure 6:
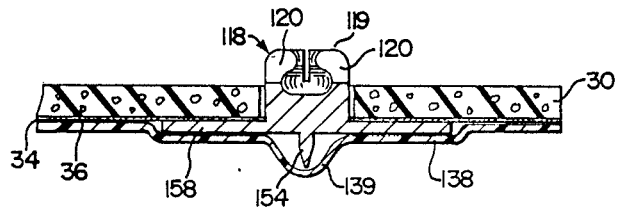
FIG. 6 is a vertical sectional view of an alternate embodiment of the patch depicted in FIG. 4.

Referring now to FIG. 6, an alternate embodiment of the electrode 18 is depicted and is generally designated 118. The electrode 118 is a one piece eyelet and needle fabricated of graphite loaded ABS plastic, and includes a female receptacle connector portion 119, a needle portion 154 and a lower flared flange end 158. The receptacle 119 is provided with multiple sections 120 which resiliently accommodate the insertion of a male lead wire connector therein. In similar fashion to the preferred embodiment, a release sheet 138 with a protective dimple 139 is provided. To produce the electrode 118, only the needle portion 154 receives the coating process described above in relation to FIGS. 4 and 5. The graphite embedded in the eyelet of the electrode 118 provides electrical continuity. The electrode 118 is secured to the patch 14 in similar fashion to the electrode 18.

Although only female receptacle configurations for the electrode connectors 19 and 119 are disclosed, male configurations are also contemplated, provided that the configuration is structurally distinguishable from the connector 17 and provides foolproof connection to the leads 20, 22 of the microprocessor unit 24.

Figure 7:
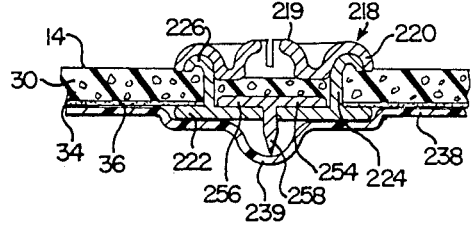
FIG. 7 is a vertical sectional view of a second alternate embodiment of the patch depicted in FIG. 4.

Referring now to FIG. 7, a second alternate embodiment of the electrode 18 is depicted and is generally designated 218. The electrode 218 includes a snap-type, electrically conductive female receptacle connector portion 219 having an upper socket 220 and an open ring 222. The open ring 222 includes vertically projecting prongs 224 which pass through the patch 14 to engage curved portions 226 in the socket 220. In similar fashion to the embodiments of FIGS. 4 and 6, a release sheet 238 with a protective dimple 239 is also provided.

The needle type glucose sensor 254 is secured against the underside 34 of the patch 14 by the ring 222 so that it depends from the patch and is physically attached to the electrode connector 219. Electrical continuity is maintained between the needle 258 and the connector portion 219 by virtue of the contacting relationship of the graphite eyelet 256 with the ring 222, and that of the prongs 224 with the curved portions 226. In this embodiment, the needle sensor 254 is attached to the female electrode connector 219, however, either male or female connector configurations may be used.

Basically, the sensor 254 includes a one-piece graphite eyelet 256 and needle 258, or a metallic needle, preferably platinum, silver or stainless steel inserted through an opening (not shown) in the eyelet 256. The needle 258 is provided with enzyme, ferrocene and polyurethane coatings as applied to the embodiments of FIGS. 4 and 6.

Referring now to FIGS. 1 and 2, the microprocessor 24 includes the two connector leads 20 and 22, each of which having a connector attachment 72, 74 at a free end, the attachments 72 and 74 being configured to matingly and releasably engage the electrode connectors 16 and 18, respectively. More specifically, the lead attachment 72 has a female configuration and the lead attachment 74 has a male configuration. Thus, the distinct structural configuration of the electrode connectors 17 and 19 ensures that the connector leads 20, 22 from the microprocessor will not be incorrectly attached thereto.

The leads 20 and 22 are connected to the internal circuitry of the microprocessor 24 which includes a conventional ammeter circuit (not shown) to receive current produced from the glucose sensor electrode needle 54 according to the following reaction:

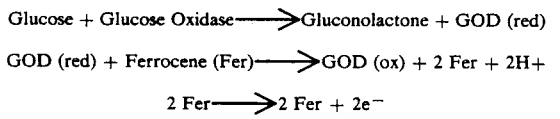

The enzyme action of the above-identified reaction creates a current flow in the order of millionths of amperes down to thousandths of a millionth of an ampere (nanoamperes). The current generated by this reaction will be transmitted through the female electrode connector 19 and lead 22 to the microprocessor unit 24, which is programmed to receive signals from the ammeter circuit and to calculate a current average value over a specified time period, such as a half hour. Once the calculation is made, it is correlated with blood glucose level, and the resulting value is displayed upon the LCD readout 28. The microprocessor 24 is preferably programmed to display the average value on a continuous basis. The LCD readout 28 then displays the blood glucose level in units of mg/dl, such as "150" or "120" in digital fashion, accompanied by an arrow 80 pointing upwardly indicating that a glucose level is increasing, a downward arrow (not shown) to indicate that the level is decreasing or a hyphen (not shown) indicating that the glucose level is remaining generally constant. If desired, the microprocessor 24 may be provided with an audible or visible alarm (not shown) which alerts the patient when sensed blood glucose levels vary from optimum preprogrammed levels.

In that the present glucose sensor 10 monitors blood glucose level at the subcutaneous layer of the skin, there will be some inherent lag time, of approximately 10–15 minutes, until a corresponding blood glucose level is sensed at the site of the needle 54. Any detrimental therapeutic effect of this lag time is minimized by the periodic averaging of sensed current values by the microprocessor 24.

Accordingly, the blood glucose sensor of the invention provides a convenient, minimally invasive system for continually monitoring blood glucose levels. In operation, the patch 14 is applied to a desired portion of the body, such as the forearm 12, by removing the release sheet 38 from the adhesive 36 on the bottom surface 34. Sufficient pressure is applied to the patch 14 so that the needle 54, 154, 254 of the glucose sensor electrode 18, 118, 218 enters the subcutaneous layer of skin. The electrode 16 contacts the surface of the skin through the conductive gel 50. Electrical contact between the microprocessor unit 24 and the patch 14 is established by the connection of the leads 20, 22 to the respective electrode connectors 17, 19, 119, 219 by the connector ends 72, 74. The blood glucose reacts with the enzyme coated needle 54, 154, 254, and generates electrical current which is transmitted to the microprocessor 24. The microprocessor then converts the current into corresponding units of glucose, averages the value over a specified time interval and displays the resulting value on the display 28. The circuit is completed by the electrode 16 and the lead 20.

While a particular embodiment of the improved blood glucose monitoring system of the invention has been shown and described, it will be appreciated by those skilled in the art that changes and modifications may be made thereto without departing from the invention in its broader aspects and as set forth in the following claims.

I claim:

1. A blood glucose monitoring system, comprising:
   a patch having a top surface, an underside and being configured for removable attachment to the skin of a patient;
   a needle type glucose sensor being secured to said patch and having a needle electrode depending from said patch underside so as to penetrate the skin of the patient;
   a second electrode secured to said patch and having a surface exposed on said underside of said path to permit electrical contact with the skin;
   a pair of structurally distinguishable electrode connectors secured to said patch, exposed at said top surface of said patch and connected to said needle electrode and said second electrode, respectively.
   processing means having a display, and positive and negative leads, each said lead having a lead end attachment positively and releasably connected only to a corresponding one of said electrode connectors, said processing means being programmed for receiving signals from said needle electrode, for calculating an average current value over a specified time period, for converting said current value into blood glucose and for displaying said value on said display.

2. The system as defined in claim 1 wherein said needle electrode is covered with an immobilized glucose oxidase coating.

3. The system as defined in claim 2 wherein said needle electrode is made of platinum.

4. The system as defined in claim 2 wherein said needle electrode is made of graphite.

5. The system as defined in claim 2 wherein said needle electrode is made of stainless steel.

6. The system as defined in claim 2 wherein said glucose oxidase coating is combined with a mediator coating on said needle electrode.

7. The system as defined in claim 6 wherein said mediator is ferrocene.

8. The system as defined in claim 1 wherein one of said electrode connectors has an upwardly projecting male configuration, and the other of said connectors has an upwardly projecting female configuration.

9. The system as defined in claim 8 wherein said female connector in integral with said needle electrode.

10. The system as defined in claim 8 wherein said male electrode connector is integral with said second electrode.

11. The system as defined in claim 1 wherein said processing means includes a wrist strap for attachment to the wrist of the patient.

12. The system as defined in claim 1 wherein said processing means has an LCD display.

13. The system as defined in claim 12 wherein said LCD display includes means for indicating the level of glucose in the blood, and whether that level is increasing, decreasing or remains constant.

14. The system as defined in claim 1 wherein said patch has an elongate slot disposed between said electrode connectors.

15. The system as defined in claim 1 wherein said patch underside is provided with an adhesive coating, and said coating is covered by a release sheet.

16. The system as defined in claim 15 wherein said release sheet is provided with a dimple portion covering a tip of said needle electrode.

17. The system as defined in claim 16 further including a second dimple formation covering said second electrode.

18. A blood glucose monitoring system, comprising:
a generally planar disposable patch having a top surface, an elongate slot and an underside, said underside being provided with an adhesive coating for releasable attachment to the skin of a patient;
a needle type glucose sensor having a needle-tipped electrode being secured to said patch so that a portion of said needle tipped electrode depends from said patch underside and enters the skin of the patient;
a second electrode secured to said underside of said patch so as to be in electrical contact with the skin, said second electrode being located on an opposite side of said slot from said needle-tipped electrode.
male and female electrode connectors secured to said patch so that portions of said connectors project vertically from said top surface, said connectors being connected to said needle-tipped and second electrodes;
processing means having a display and positive and negative leads for connection to said respective electrode connectors, said leads having end attachments releasably and positively connected to said connectors in a specified manner only, said processing means being programmed for receiving signals from said electrodes, for calculating an average current value over a specified time period, for converting said current value into blood glucose units, and for displaying said value.

19. The system as defined in claim 18 wherein said needle-tipped electrode is provided with coatings of glucose oxidase and a ferrocene mediator.

20. The system as defined, in claim 18 wherein said processing means lead end attachment are configured to be connected to only one of said electrode connectors.

21. The, system as defined in claim 18 wherein said needle-tipped electrode is secured to said patch by a plastic eyelet.

22. The system as defined in claim 21 wherein said needle-tipped electrode is integral with said eyelet.

23. The system as defined in claim 18 wherein said needle-tipped electrode is secured to said patch by a two-piece snap assembly.

24. The system as defined in claim 18 further including a release sheet covering said adhesive coating, said release sheet having a dimple formation for covering said needle-tipped electrode portion.

25. The system as defined in claim 24 further including a second dimple formation on said release sheet covering said second electrode.

26. A disposable electrode patch for a blood glucose monitoring system including a microprocessor having a display, and positive and negative leads, the leads each having an end attachment, the microprocessor being programmed for receiving signals, for calculating an average current value over a specified time period, for converting the current value into blood glucose and for displaying the value on the display, the patch comprising:
a body with a top surface, an underside and being configured for removable attachment to the skin of a patient;
a needle type glucose sensor being secured to said body and having a needle electrode depending from said body underside so as to penetrate the skin of the patient;
a second electrode secured to said body and having a surface exposed on said body underside to permit electrical contact with the skin; and
a pair of structurally distinguishable electrode connectors secured to said body, exposed at said top surface of said body and connected to said needle electrode and said second electrode, respectively, said connectors being configured for positive electrical connection to the leads of the microprocessor for sending signals thereto.

* * * * *